(12) United States Patent
Wierzbicki et al.

(10) Patent No.: US 8,404,742 B2
(45) Date of Patent: Mar. 26, 2013

(54) DIOSMETIN COMPOUNDS, A PROCESS FOR THEIR PREPARATION AND PHARMACEUTICAL COMPOSITIONS CONTAINING THEM

(75) Inventors: Michel Wierzbicki, L'etang la Villa (FR); Marie-Francoise Boussard, Mareil sur Mauldre (FR); Tony Verbeuren, Vernouillet (FR); Patricia Sansilvestri-Morel, Antony (FR); Alain Rupin, Savonnieres (FR); Jérôme Paysant, Garches (FR); François Lefoulon, Orleans (FR)

(73) Assignee: Les Laboratoires Server, Suresnes Cedex (FR)

( * ) Notice: Subject to any disclaimer, the term of this patent is extended or adjusted under 35 U.S.C. 154(b) by 0 days.

(21) Appl. No.: 13/372,811

(22) Filed: Feb. 14, 2012

(65) Prior Publication Data
US 2012/0208777 A1    Aug. 16, 2012

Related U.S. Application Data

(62) Division of application No. 12/383,888, filed on Mar. 30, 2009, now Pat. No. 8,138,223.

(30) Foreign Application Priority Data

Apr. 1, 2008   (FR) ..................... 08 01779

(51) Int. Cl.
*A01N 43/16*   (2006.01)
*A61K 31/35*   (2006.01)
(52) U.S. Cl. ............... 514/456; 514/35; 514/27
(58) Field of Classification Search ............ 514/456, 514/27, 35
See application file for complete search history.

(56) References Cited

U.S. PATENT DOCUMENTS 5,792,789 A    8/1998   Wierzbicki et al. ............ 514/456

FOREIGN PATENT DOCUMENTS

| EP | 0709383 | 5/1996 |
|---|---|---|
| WO | 2006092490 | 9/2006 |

OTHER PUBLICATIONS

French Preliminary Search Report for FR200801779 of Oct. 20, 2008.

*Primary Examiner* — Brandon Fetterolf
*Assistant Examiner* — Jean Cornet
(74) *Attorney, Agent, or Firm* — Hueschen and Sage

(57) ABSTRACT

Compounds of formula (I):

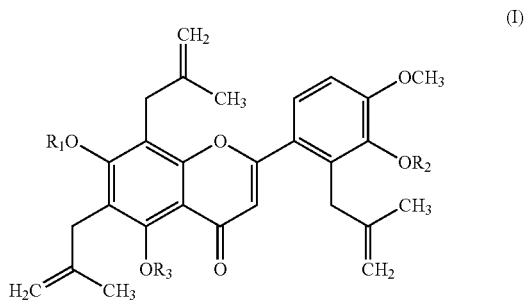

wherein $R_1$, $R_2$ and $R_3$, which may be the same or different, each represent a hydrogen atom or the group of formula (A):

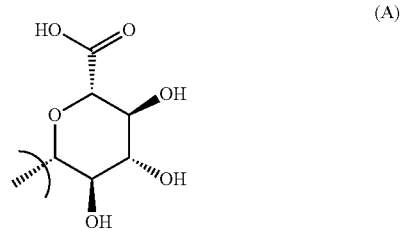

Medicinal products containing the same which are useful in the prevention and/or treatment of venous diseases and other conditions.

7 Claims, No Drawings

DIOSMETIN COMPOUNDS, A PROCESS FOR THEIR PREPARATION AND PHARMACEUTICAL COMPOSITIONS CONTAINING THEM

The present invention relates to new diosmetin compounds, to a process for their preparation and to pharmaceutical compositions containing them.

Diosmetin compounds and their activity in the treatment of venous insufficiency have been described in the patent specification EP 0 709 383.

The compounds of the invention are adhesion molecule inhibitors, NADPH oxidase inhibitors and anti-platelet aggregation agents.

The properties of leukocyte adhesion inhibition and NADPH oxidase inhibition are important in the treatment of chronic venous disease in consideration of the fact that, in this pathology, inflammation of the microcirculatory network of the lower limbs involving leukocyte infiltrations has been widely described (Verbeuren T J, Bouskela E, Cohen R A et al., *Regulation of adhesion molecules: a new target for the treatment of chronic venous insufficiency*, 2000, Microcirculation, 7, S41-S48).

The property of platelet aggregation inhibition demonstrates the anti-thrombotic potential of the compounds of the invention, not only in the prevention and treatment of venous and arterial thromboses but also in the treatment of chronic venous disease, where the platelets can be activated by inflammatory mediators, or in patients having a post-thrombotic syndrome.

The presence of capillary/venule microangiopathy has been demonstrated in chronic venous diseases. This microangiopathy is the consequence of venous hypertension and causes problems with capillary/venule filtration (hyperpermeability) and, therefore, micro-oedemas (Barbier et al., *Microcirculation and rheology*, 1994, Presse med. 23, 213-224). Numerous studies have shown the involvement of endothelial cell activation in venous hypertension associated with an increase in circulating levels of adhesion molecules (Saharay M, Shields D A, Georgiannos S N et al., *Endothelial activation in patients with chronic venous disease*, 1998, Eur J Vasc Surg, 15, 342-349; Verbeuren T J, Bouskela E, Cohen R A et al., *Regulation of adhesion molecules: a new target for the treatment of chronic venous insufficiency*, 2000, Microcirculation, 7, S41-S48). The compounds of the present invention have not only anti-inflammatory activity but also anti-hyperpermeability activity.

Furthermore, an increase in free radicals and therefore activation of NADPH oxidase has been demonstrated in chronic venous diseases. This oxidative stress is thought to be linked to endothelial cell activation and leukocyte infiltration (Glowinski J and Glowinski S, *Generation of reactive oxygen metabolites by the varicose vein wall*, 2002, Eur. J. Vasc. Endovasc. Surg., 23, 5550-555).

Endothelial cell infiltration and induction of adhesion molecules and of NADPH oxidase has been demonstrated in a number of vascular pathologies (Bedard K and Krause K H, *The NOX family of ROS-generating oxidases: Physiology and pathophysiology*, 2007, Physiol. Rev. 87, 245-313).

Accordingly, the compounds of the present invention can be used in the prevention or treatment of venous diseases, especially chronic venous disease in all its stages (pain, telangiectasia, varicose veins, oedemas, trophic disorders, ulcers) and also in the prevention or treatment of post-thrombotic syndrome, vascular complications associated with diabetes, hypertension, atherosclerosis, inflammation, metabolic syndrome associated with obesity, vascular complications associated with obesity, angina pectoris, arteritis of the lower limbs or cerebral vascular accidents, healing of chronic wounds including mainly venous or mixed leg ulcers and diabetic foot, in the treatment or prevention of hemorrhoid attacks, in the treatment or prevention of pressure ulcers and in the treatment of multiple sclerosis.

More specifically, the present invention relates to compounds of formula (I):

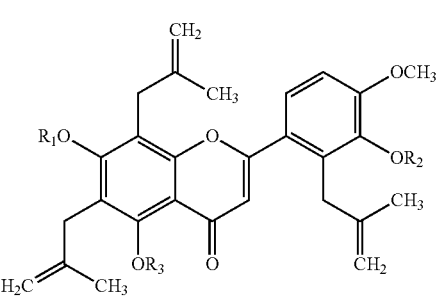

wherein $R_1$, $R_2$ and $R_3$, which may be the same or different, each represent a hydrogen atom or the group of formula (A):

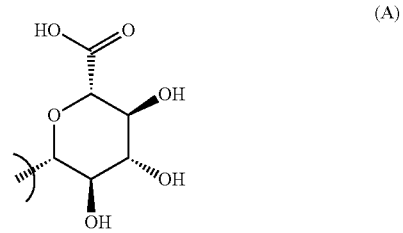

Compounds wherein at least one of $R_1$, $R_2$ and $R_3$ represents a group (A) are metabolites of the compound of formula (Ia), wherein $R_1$, $R_2$ and $R_3$ each represent a hydrogen atom.

The present invention relates also to a process for the preparation of compounds of formula (I), starting from diosmetin of formula (II):

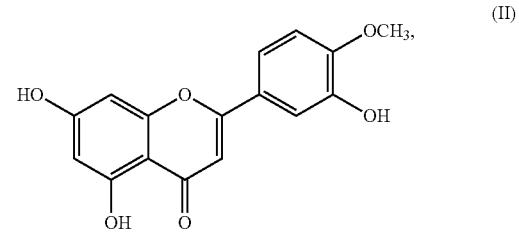 [SMILES: COc1ccc(-c2cc(=O)c3c(O)cc(O)cc3o2)cc1O]

which is reacted with methallyl bromide to yield the compound of formula (III):

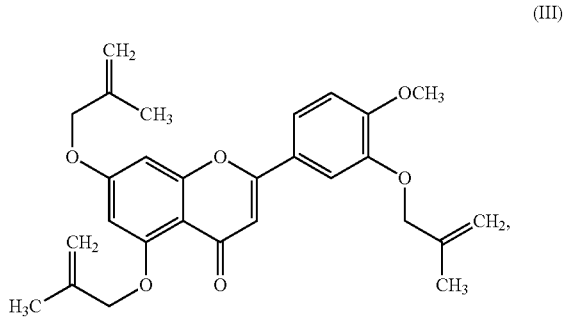 [SMILES: C=C(C)COc1cc(OCC(=C)C)c2c(=O)cc(-c3ccc(OC)c(OCC(=C)C)c3)oc2c1]

which is heated to yield the compound of formula (Ia), a particular case of the compounds of formula (I) wherein $R_1$, $R_2$ and $R_3$ each represent a hydrogen atom:

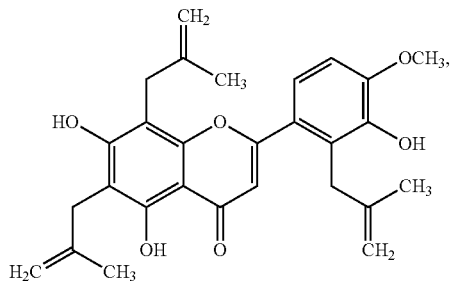

(Ia)

which, when it is desired to obtain other compounds of formula (I), is reacted with the compound of formula (IV):

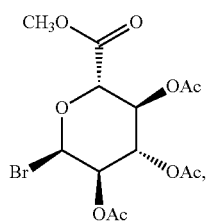

(IV)

wherein Ac represents the acetyl group, to yield, after deprotection of the acid function and the alcohol functions of the group (A), the compounds of formula (I) wherein at least one of $R_1$, $R_2$ and $R_3$ is other than H.

When compounds of formula (I) are obtained in admixture, they may be separated, for example by preparative HPLC chromatography.

The compound of formula (Ib), wherein $R_1$ and $R_3$ each represent a hydrogen atom and $R_2$ represents a group of formula (A), can also be obtained by acetylation of the compound of formula (Ia) to yield the compound of formula (V):

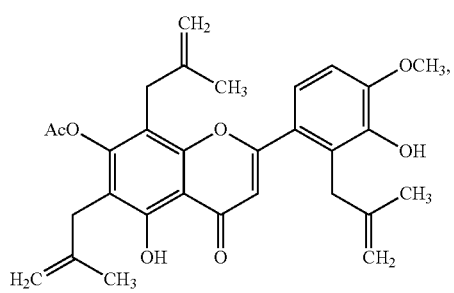

(V)

wherein Ac represents the acetyl group, which is reacted with the compound of formula (IV) to yield the compound of formula (VI):

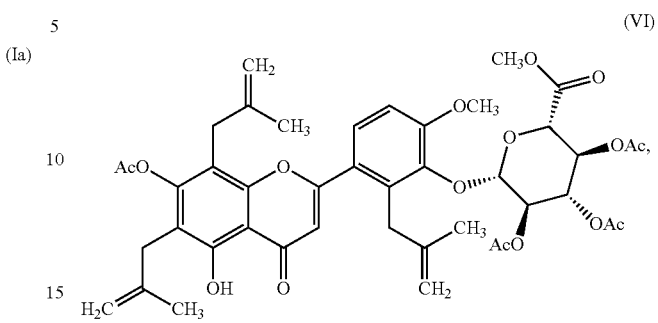

(VI)

wherein Ac represents the acetyl group,
the acid function and alcohol and phenol functions of which are deprotected to yield the compound of formula (Ib).

The compounds of the invention are adhesion molecule and NADPH oxidase inhibitors and anti-platelet aggregation agents.

By virtue thereof they are useful in the prevention or treatment of venous diseases, especially chronic venous disease in all its stages (pain, telangiectasia, varicose veins, oedemas, trophic disorders, ulcers) and also in the prevention or treatment of post-thrombotic syndrome, vascular complications associated with diabetes, hypertension, atherosclerosis, inflammation, metabolic syndrome associated with obesity, vascular complications associated with obesity, angina pectoris, arteritis of the lower limbs or cerebral vascular accidents, healing of chronic wounds including mainly venous or mixed leg ulcers and diabetic foot, in the treatment or prevention of hemorrhoid attacks, in the treatment or prevention of pressure ulcers and in the treatment of multiple sclerosis.

The present invention relates also to pharmaceutical compositions comprising as active ingredient a compound of formula (I), in combination with one or more pharmaceutically acceptable, non-toxic, inert carriers or excipients.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially tablets or dragées, sublingual tablets, hard gelatin capsules, capsules, suppositories, creams, ointments, dermal gels, injectable or drinkable preparations, aerosols, eye drops and nose drops.

In addition to the compound of formula (I), the pharmaceutical compositions according to the invention comprise one or more excipients or carriers such as diluents, lubricants, binders, disintegrating agents, absorbents, colourants, sweeteners.

By way of example of excipients or carriers, there may be mentioned:
  as diluents: lactose, dextrose, sucrose, mannitol, sorbitol, cellulose, glycerol,
  as lubricants: silica, talc, stearic acid and its magnesium and calcium salts, polyethylene glycol,
  as binders: aluminium silicate, magnesium silicate, starch, gelatin, tragacanth, methylcellulose, sodium carboxymethylcellulose and polyvinylpyrrolidone,
  as disintegrating agents: agar, alginic acid and its sodium salt, effervescent mixtures.

The percentage of active ingredient of formula (I) in the pharmaceutical composition is preferably from 5% to 50% by weight.

The useful dosage varies according to the age and weight of the patient, the administration route, the nature and severity of the disorder, and the administration of any associated treatments and ranges from 0.5 mg to 1000 mg per day in one or more administrations.

The Examples that follow illustrate the present invention. The structures of the compounds described in the Examples were determined according to customary spectrophotometric techniques (infrared, nuclear magnetic resonance, mass spectrometry).

| ABBREVIATIONS | |
|---|---|
| DMSO: | dimethyl sulphoxide |
| NADPH: | reduced form of Nicotinamide Adenine Dinucleotide Phosphate |
| HPLC: | High-Performance Liquid Chromatography |

EXAMPLE 1

6,8,2'-Tris(isobut-2-en-1-yl)diosmetin

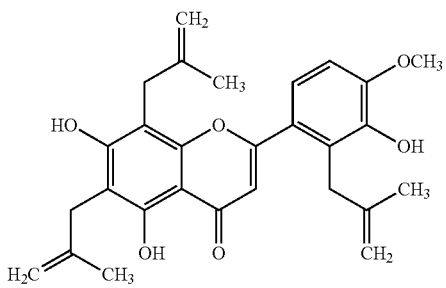 [SMILES: C=C(C)Cc1c(-c2cc(=O)c3c(O)c(CC(=C)C)c(O)c(CC(=C)C)c3o2)ccc(OC)c1O]

Step A: 2-{4-Methoxy-3-[(isobut-2-en-1-yl)oxy]phenyl}-5,7-bis[(isobut-2-en-1-yl)oxy]-4H-chromen-4-one To 30 g of diosmetin there are added 69.3 g of potassium carbonate and 450 ml of acetone. The mixture is heated at reflux for 4 hours 30 minutes and then returned to ambient temperature; 54 g of methallyl bromide are then added. The reaction mixture is then heated at reflux overnight and then returned to ambient temperature and filtered. The filter cake is rinsed with acetone and then the filtrate is evaporated to yield a residue which is recrystallised from toluene to yield the title compound.

Step B: 6,8,2'-Tris(isobut-2-en-1-yl)diosmetin

To 10 g of the compound obtained in the previous Step there are added 120 ml of N,N-dimethylaniline; the mixture is then heated at reflux for 1 hour. The solvent is then evaporated off under reduced pressure and the residue obtained is recrystallised from isopropanol to yield the title compound.

Melting point: 141° C.

EXAMPLE 2

(5-Hydroxy-2-[3-hydroxy-4-methoxy-2-(isobut-2-en-1-yl)phenyl]-6,8-bis(isobut-2-en-1-yl)-4-oxo-4H-chromen-7-yl)-beta-D-glucuronic acid

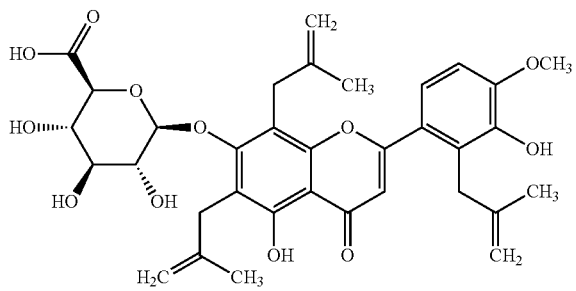 [SMILES: C=C(C)Cc1c(-c2cc(=O)c3c(O)c(CC(=C)C)c(O[C@@H]4O[C@H](C(=O)O)[C@@H](O)[C@H](O)[C@H]4O)c(CC(=C)C)c3o2)ccc(OC)c1O]

Step A: Methyl 5-hydroxy-2-[3-hydroxy-4-methoxy-2-(isobut-2-en-1-yl)phenyl]-6,8-bis(isobut-2-en-1-yl)-4-oxo-4H-chromen-7-yl-2,3,4-tris-O-acetyl-beta-D-glucuronate The title compound is obtained by reacting the compound of Example 1 (250 mg) with the compound of formula (IV) (429 mg), by phase transfer catalysis, according to the procedure described in the publication *Synth Commun* 1999, 29(16), 2775-2781.

Step B: (5-Hydroxy-2-[3-hydroxy-4-methoxy-2-(isobut-2-en-1-yl)phenyl]-6,8-bis(isobut-2-en-1-yl)-4-oxo-4H-chromen-7-yl)-beta-D-glucuronic acid The compound obtained in Step A is dissolved in methanol, and then sodium hydroxide is added. The mixture is refluxed for 1 hour 30 minutes and then neutralised with 2N hydrochloric acid solution before being evaporated to dryness to yield the title compound.

EXAMPLE 3

3-[5,7-Dihydroxy-6,8-bis(isobut-2-en-1-yl)-4-oxo-4H-chromen-2-yl]-6-methoxy-2-(isobut-2-en-1-yl)phenyl-beta-D-glucuronic acid

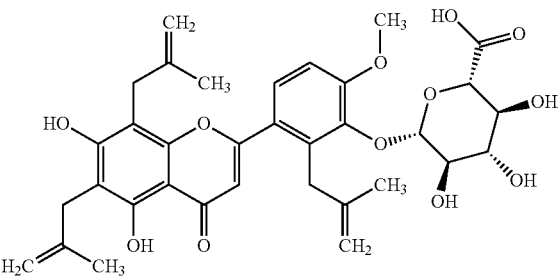 [SMILES: C=C(C)Cc1c(-c2cc(=O)c3c(O)c(CC(=C)C)c(O)c(CC(=C)C)c3o2)ccc(OC)c1O[C@@H]1O[C@H](C(=O)O)[C@@H](O)[C@H](O)[C@H]1O]

Step A: 5-Hydroxy-2-[3-hydroxy-4-methoxy-2-(isobut-2-en-1-yl)phenyl]-6,8-bis(isobut-2-en-1-yl)-4-oxo-4H-chromen-7-yl acetate The compound of Example 1 (3 g) is dissolved in pyridine, and then acetic anhydride (0.61 ml) is added at ambient temperature. The reaction mixture is then stirred for 16 hours and subsequently evaporated to dryness. The residue is taken up in ice-cold water and then extracted with dichloromethane, dried, filtered and evaporated. The crude product thereby obtained is purified on silica gel and then by reverse-phase preparative HPLC to yield the title compound.

Step B: Methyl 3-[7-(acetyloxy)-5-hydroxy-6,8-bis(isobut-2-en-1-yl)-4-oxo-4H-chromen-2-yl]-6-methoxy-2-(isobut-2-en-1-yl)phenyl-2,3,4-tris-O-acetyl-beta-D-glucuronate Starting from the compound obtained in the previous Step, the title compound is obtained according to the procedure of Step A of Example 2.

Step C: 3-[5,7-Dihydroxy-6,8-bis(isobut-2-en-1-yl)-4-oxo-4H-chromen-2-yl]-6-methoxy-2-(isobut-2-en-1-yl)phenyl-beta-D-glucuronic acid Starting from the compound obtained in the previous Step, the title compound is obtained according to the procedure of Step B of Example 2.

Pharmacological Study

In the Examples that follow, the term "reference compound" refers to Example 69 of EP 0 709 383.

EXAMPLE 4

In Vitro Inhibition of Platelet Aggregation

A sample of blood is drawn off from anaesthetised New Zealand rabbits, from the carotid artery, over 0.109M citrate. The platelet-rich plasma is obtained by centrifugation. The platelets are then washed by centrifugation.

The washed platelets are resuspended in a Tyrode buffer. The platelet suspension is placed in a cell and then in an aggregometer at 37° C., with stirring, in the presence of the compound of Example 1 (30 μM) or the reference compound (30 μM), each diluted in the same solvent (0.1% DMSO). After 2 minutes, aggregation is brought about using collagen (4 μg/ml); the response is then recorded for 6 minutes. Platelet aggregation is quantified by means of turbidimetry, that is to say the percentage light that is transmitted through the platelet suspension with respect to a cell containing Tyrode and a cell containing the solvent (0.1% DMSO).

The anti-aggregation efficacy of the diosmetin compounds according to the invention and, especially, of the compound of Example 1, and of the reference compound is evaluated as a function of the percentage inhibition of platelet aggregation, the larger the percentage inhibition the greater the activity. The compound of Example 1 (30 μM) causes inhibition of 36.6±9.9% whereas the reference compound does not cause a significant effect (4.1±1.8%); (P<0.01 compound of Example 1 relative to the reference compound, Student's t test, n=7).

This test demonstrates the anti-platelet aggregation activity and, therefore, the anti-thrombotic potential of the compound of Example 1.

EXAMPLE 5

In Vivo Inhibition of Leukocyte Adhesion

Three groups of 3 hamsters, weighing from 90 to 110 g, are used in this study. Thirty minutes before anaesthesia, the hamsters are treated orally with a single dose of placebo (gum arabic 10%), of compound of Example 1 (3 mg/kg) or of reference compound (3 mg/kg). The animals are anaesthetised with pentobarbital 50 mg/kg by intraperitoneal administration. The hamsters are placed under a microscope and the cheek pouch is isolated and immersed in a perfusion solution (NaCl 110.0 mM, KCl 4.7 mM, $CaCl_2$ 2.0 mM, $MgSO_4$ 1.2 mM, $NaHCO_3$ 18.0 mM, Hepes 15.39 mM and Hepes $Na^+$-salt 14.61 mM), (Duling, *The preparation and use of the hamster cheek pouch for studies of the microcirculation,* 1973, Microvasc. Res. 5: 423-429; Svensjö et al., *The hamster cheek pouch preparation as a model for studies of macromolecular permeability of the microvasculature,* 1978, Uppsala J. Med. Sci. 83: 71-79).

Local ischaemia is brought about with the aid of a latex tube fitted at the entrance to the cheek pouch. The intratubular pressure of the tube is increased to 200-220 mm Hg with the aid of a calibrated syringe. This total occlusion is carried out for 30 minutes and then reperfusion is performed for 45 minutes. Leukocyte adhesion to the endothelial cells in the post-capillary venules is quantified in a field of 6 $mm^2$ immediately after the start of ischaemia (defined as 100%) and then at different times after reperfusion (0, 15, 30 and 45 minutes).

The model of leukocyte adhesion, brought about by ischaemia reperfusion, in the hamster cheek pouch makes it possible to confirm the efficacy of the diosmetin compounds according to the invention as anti-adhesion agents, especially the compound of Example 1 and the reference compound.

The activity of the compound of Example 1 and the reference compound is evaluated as a function of the number of leukocytes adhering to endothelial cells for a field of 6 $mm^2$ after ischaemia/reperfusion, that activity being greater the lower the number of leukocytes and, therefore, the lower the percentage of adhering leukocytes relative to the number of adhering leukocytes after ischaemia.

TABLE 1

Effect of oral treatment of hamsters with the compound of Example 1 or the reference compound on the number of leukocytes adhering to endothelial cells in post-capillary venules of the cheek pouch, after ischaemia (number of leukocytes considered as 100%) and after 0, 15, 30 and 45 minutes of reperfusion.

| Time after reperfusion (minutes) | Placebo | Compound of Example 1 | Reference compound |
| --- | --- | --- | --- |
| 0 | 165.8 ± 12.8% | 81.7 ± 19.1%** | 129.3 ± 10.9% |
| 15 | 211.8 ± 11.6% | 100 ± 13.7%*** | 138.0 ± 14.4%** |
| 30 | 210.5 ± 16.6% | 91.0 ± 18.7%*** | 121.0 ± 18.0%** |
| 45 | 166.3 ± 11.1% | 109.3 ± 23.0% | 133.7 ± 42.4% |

**$p < 0.01$;
***$p < 0.001$ relative to the placebo treatment, 2-factor (time and treatment) ANOVA, followed by a Bonferroni test (n = 3).

The compound of Example 1 makes it possible to clearly and significantly reduce the number of leukocytes adhering to endothelial cells after ischaemia/reperfusion relative to the placebo. The activity of the compound of Example 1 is more potent than that of the reference compound.

This test demonstrates the inhibitory activity, on leukocyte adhesion, of the compound of Example 1 and therefore the potential for treatment of venous disease and also arterial vascular diseases such as atherosclerosis or vascular complications associated with diabetes.

EXAMPLE 6

In Vivo Inhibition of the Expression of Vascular Cell Adhesion Molecule 1 (VCAM-1)

Four groups of 8 mice deficient in apolipoprotein E (ApoE$^{-/-}$, spontaneously developing atheroma plaques in their aortas) are used in this study. At the age of 9 weeks, the mice are made diabetic by 5 intraperitoneal injections of 100 mg/kg of streptozotocin over 5 days. At the tenth week, the animals are divided into four groups: compound of Example 1 control group, compound of Example 1 treatment group (130 mg/kg/day in the food for 6 weeks), reference compound control group, reference compound treatment group (130 mg/kg/day in the food for 6 weeks). The mice are sacrificed at the fifteenth week after anaesthesia using isoflurane. The aortas are removed, dissected and frozen in liquid nitrogen. The aortas are cryo-ground, and total RNA is extracted using the RNeasy® micro kit (Qiagen). Reverse transcription is then performed on 1 µg of total RNA using the Superscript™ III first-strand cDNA synthesis kit (Invitrogen). Expression of VCAM-1 is quantified by real-time PCR and normalised with respect to 3 reference genes: β-actin, hypoxanthine-guanine phosphoribosyl transferase (HPRT) and glyceraldehyde phosphate dehydrogenase (GAPDH). The IQ™ SYBR®Green supermix kit (Biorad) is used, with 2 µl of cDNA and 150 nM of each primer. The samples are denatured for 5 minutes at 95° C. and amplified for 40 cycles in accordance with the following protocol: denaturation for 20 seconds at 95° C. and hybridisation and elongation for 1 minute at 54° C. for VCAM-1, β-actin and HPRT, and at 56° C. for GAPDH. The threshold cycle (defined as the cycle for which the fluorescence is considered to be significantly higher than the background noise) for VCAM-1 of the untreated animals is normalised with respect to the reference genes (and considered to be 100%) and then compared to that of the treated animals.

The specific primers used are as follows:

```
VCAM-1:
                                   (SEQ ID NO: 1)
5'-AGA GCA GAC TTT CTA TTT CAC-3' (sense)
and
                                   (SEQ ID NO: 2)
5'-CCA TCT TCA CAG GCA TTT C-3' (antisense);

β-actin:
                                   (SEQ ID NO: 3)
5'-AAG ACC TCT ATG CCA ACA CAG-3' (sense)
and
                                   (SEQ ID NO: 4)
5'-AGC CAC CGA TCC ACA CAG-3' (antisense);

HPRT:
                                   (SEQ ID NO: 5)
5'-AGC TAC TGT AAT GAT CAG TCA ACG-3' (antisense);

GAPDH:
                                   (SEQ ID NO: 6)
5'-GCC TTC CGT GTT CCT ACC C-3' (sense)
and
                                   (SEQ ID NO: 7)
5'-TGC CTG CTT CAC CAC CTT-3' (antisense).
```

The model of bringing about diabetes in mice that are deficient in ApoE makes it possible to confirm the efficacy of the diosmetin compounds according to the invention as anti-adhesion agents.

The activity of the compound of Example 1 and of the reference compound is evaluated as a function of the level of VCAM-1 expression in the aorta, compared to the untreated animals, this activity being greater the lower the level of VCAM-1 expression. The mice treated with the compound of Example 1 have a level of VCAM-1 expression of 65.9±10.1% relative to the untreated mice (P<0.01, Student's t test, n=8), whereas those treated with the reference compound have a level of VCAM-1 expression of 83.0±6.6% (P<0.05, Student's t test, n=8). The compound of Example 1 makes it possible to clearly and significantly reduce the expression of VCAM-1 in the aorta of diabetic ApoE$^{-/-}$ mice relative to the untreated group. The activity of the compound of Example 1 is more potent than that of the reference compound.

This test demonstrates the inhibitory activities, on the expression of adhesion molecules, of the compound of Example 1 and therefore the potential for treatment of venous disease and also in arterial pathologies, such as vascular complications associated with diabetes, hypertension, atherosclerosis, inflammation, metabolic syndrome associated with obesity, vascular complications associated with obesity, angina pectoris, arteritis of the lower limbs and cerebral vascular accidents.

EXAMPLE 7

In Vitro Inhibition of the Activity of NADPH Oxidase

The study is carried out on human endothelial cells HUVEC (Human Umbilical Vein Endothelial Cells, Clonetics Co). The cells are cultured in an EBM2 medium (Endothelial Basal Medium, Clonetics Co) supplemented with 2% FCS (Fœtal Calf Serum) and EGM2 (Endothelial Growth Medium, Clonetics Co).

The cells are incubated in the presence of solvent (0.1% DMSO, compound of Example 1 control), EBM2 (compound of Example 2 control and compound of Example 3 control), compound of Example 1 (100 µM), compound of Example 2 (100 µM) or compound of Example 3 (100 µM) for 15 minutes and then activated using angiotensin II (1 µM) for 30 minutes in order to activate the NADPH oxidase. The cells are washed with EBM2, and then the NADPH oxidase substrate (NADPH, 200 µM) and lucigenin (25 µM) are added. The reduction in lucigenin by the superoxide anions produced by the NADPH oxidase is quantified using a luminometer. The number of counts per second (cps) of the control groups is compared to the treatment groups. The cps obtained with the control groups are considered as 100% NADPH oxidase activity.

The model of measuring the endothelial NADPH oxidase activity brought about by angiotensin II makes it possible to confirm the efficacy of the diosmetin compounds according to the invention as agents that are inhibitors of NADPH oxidase activity.

The activity of the compounds of Examples 1, 2 and 3 is evaluated as a function of the number of cps obtained, that activity being greater the lower the number of cps.

TABLE 3

Effect of treatment of human endothelial cells with the compounds of Examples 1, 2 and 3 on NADPH oxidase activity after induction using angiotensin II (activity of the control group [without compound] being considered as 100%).

| Group | NADPH oxidase activity (%/control group) |
|---|---|
| Compound of Example 1 control group | 100% |
| Compound of Example 1 treatment group (100 μM) | 38.16 ± 3.13%*** |
| Compound of Example 2 & 3 control group | 100% |
| Compound of Example 2 treatment group (100 μM) | 30.60 ± 4.83%*** |
| Compound of Example 3 treatment group (100 μM) | 18.45 ± 4.08%*** |

***$p < 0.01$ relative to the compound of Example 1 control group or the compound of Example 2 & 3 control group, Student's t test (n = 3).

The compounds of Examples 1, 2 and 3 make it possible to clearly and significantly reduce NADPH oxidase activity in human endothelial cells.

This test demonstrates the inhibitory activities, on vascular NADPH oxidase activity, of the compounds of Examples 1, 2 and 3 and therefore the potential for inhibiting free radicals in venous disease and also in arterial pathologies such as atherosclerosis, hypertension, vascular complications associated with diabetes and ischaemic diseases.

EXAMPLE 8

Pharmaceutical Composition

Formula for the preparation of 1000 tablets, each containing 10 mg of active ingredient:

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

---

The invention claimed is:

1. A method of treating a living animal body, including a human, afflicted with a condition selected from venous diseases and post-thrombotic syndrome, such method comprising the step of administering to the living animal body, including a human, a therapeutically effective amount of a compound selected from those of formula (I):

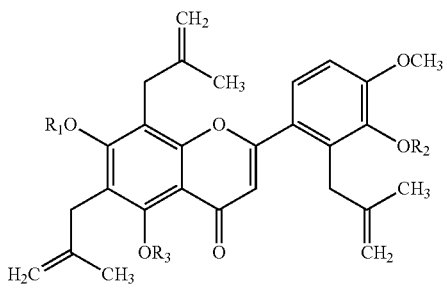

(I)

wherein $R_1$, $R_2$ and $R_3$, which may be the same or different, each represent a hydrogen atom or the group of formula (A):

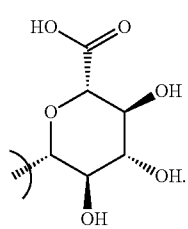

(A)

2. The method of claim 1, wherein the compound of Formula (I) is selected from:

6,8,2'-tris(isobut-2-en-1-yl)diosmetin, (5-hydroxy-2-[3-hydroxy-4-methoxy-2-(isobut-2-en-1-yl)phenyl]-6,8-bis(isobut-2-en-1-yl)-4-oxo-4H-chromen-7-yl)-beta-D-glucuronic acid, and 3-[5,7-dihydroxy-6,8-bis(isobut-2-en-1-yl)-4-oxo-4H-chromen-2-yl]-6-methoxy-2-(isobut-2-en-1-yl)phenyl-beta-D-glucuronic acid.

3. A method of treating a living animal body, including a human, afflicted with chronic venous disease, such method comprising the step of administering to the living animal body, including a human, a therapeutically effective amount of a compound selected from those of formula (I):

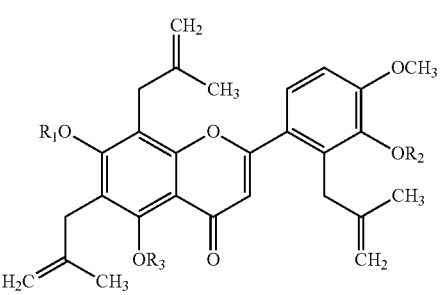

(I)

wherein $R_1$, $R_2$ and $R_3$, which may be the same or different, each represent a hydrogen atom or the group of formula (A):

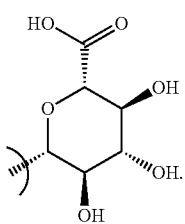

(A)

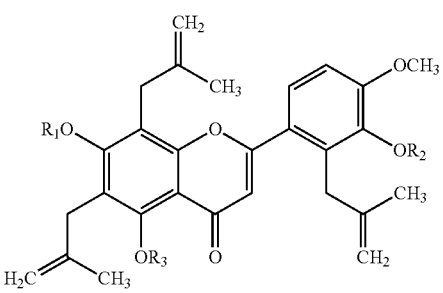

Wherein $R_1$, $R_2$ and $R_3$, which may be the same or different, each represent a hydrogen atom or the group of formula (A):

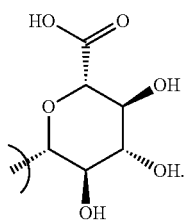

(A)

4. The method of claim 3, wherein the compound of formula (I) is selected from:
   6,8,2'-tris(isobut-2-en-1-yl)diosmetin,
   (5-hydroxy-2-[3-hydroxy-4-methoxy-2-(isobut-2-en-1-yl)phenyl]-6,8-bis(isobut-2-en-1-yl)-4-oxo-4H-chromen-7-yl)-beta-D-glucuronic acid, and
   3-[5,7-dihydroxy-6,8-bis(isobut-2-en-1-yl)-4-oxo-4H-chromen-2-yl]-6-methoxy-(isobut-2-en-1-yl)phenyl-beta-D-glucuronic acid.

5. The method of claim 1, wherein the venous disease is arteritis of the lower limbs.

6. A method of treating a living animal body, including a human, afflicted with a condition regulated by inhibition of VCAM-1 expression or by inhibition of NADPH oxidase activity selected from vascular complications associated with diabetes or obesity, hypertension, atherosclerosis, inflammation, metabolic syndrome associated with obesity, angina, pectoris, haemorrhoid attacks, and multiple sclerosis, such method comprising the step of administering to the living animal body, including a human, a therapeutically effective amount of a compound selected from those of formula (I):

7. The method of claim 6, wherein the compound of formula (I) is selected from:
   6,8,2'-tris(isobut-2-en-1-yl)diosmetin,
   (5-hydroxy-2-[3-hydroxy-4-methoxy-2-(isobut-2-en-1-yl)phenyl]-6,8~bis(isobut-2-en-1-yl)-4-oxo-4H-chromen-7-yl)-beta-D-glucuronic acid, and
   3-[5,7-dihydroxy-6,8-bis(isobut-2-en-1-yl)-4-oxo-4H-chromen-2-yl]-6-methoxy-2-(isobut-2-en-1-yl)phenyl-beta-D-glucuronic acid.

* * * * *

UNITED STATES PATENT AND TRADEMARK OFFICE
CERTIFICATE OF CORRECTION

| | |
|---|---|
| PATENT NO. | : 8,404,742 B2 |
| APPLICATION NO. | : 13/372811 |
| DATED | : March 26, 2013 |
| INVENTOR(S) | : Michel Wierzbicki et al. |

It is certified that error appears in the above-identified patent and that said Letters Patent is hereby corrected as shown below:

Title Page, Item (73) Assignee: "Les Laboratories Server" Should be --Les Laboratoires Servier--.

Signed and Sealed this
Twenty-first Day of May, 2013

Teresa Stanek Rea
*Acting Director of the United States Patent and Trademark Office*

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Completely synthesized DNA primer

<400> SEQUENCE: 1
agagcagact ttctatttca c                                              21

<210> SEQ ID NO 2
<211> LENGTH: 19
<212> TYPE: DNA
<213> ORGANISM: Artificial Sequence
<220> FEATURE:
<223> OTHER INFORMATION: Completely synthesized DNA primer

<400> SEQUENCE: 2
ccatcttcac aggcatttc                                                 19

<210> SEQ ID NO 3
<211> LENGTH: 21
<212> TYPE: DNA
<213> ORGANISM: Artificial Sequence
<220> FEATURE:
<223> OTHER INFORMATION: Completely synthesized DNA primer

<400> SEQUENCE: 3
aagacctcta tgccaacaca g                                              21

<210> SEQ ID NO 4
<211> LENGTH: 18
<212> TYPE: DNA
<213> ORGANISM: Artificial Sequence
<220> FEATURE:
<223> OTHER INFORMATION: Completely synthesized DNA primer

<400> SEQUENCE: 4
agccaccgat ccacacag                                                  18

```
<210> SEQ ID NO 5
<211> LENGTH: 24
<212> TYPE: DNA
<213> ORGANISM: Artificial Sequence
<220> FEATURE:
<223> OTHER INFORMATION: Completely synthesized DNA primer

<400> SEQUENCE: 5
agctactgta atgatcagtc aacg                                          24

<210> SEQ ID NO 6
<211> LENGTH: 19
<212> TYPE: DNA
<213> ORGANISM: Artificial Sequence
<220> FEATURE:
<223> OTHER INFORMATION: Completely synthesized DNA primer

<400> SEQUENCE: 6
gccttccgtg ttcctaccc                                                19

<210> SEQ ID NO 7
<211> LENGTH: 18
<212> TYPE: DNA
<213> ORGANISM: Artificial Sequence
<220> FEATURE:
<223> OTHER INFORMATION: Completely synthesized DNA primer

<400> SEQUENCE: 7
tgcctgcttc accacctt                                                 18
```